US012767779B2

(12) United States Patent
Gu

(10) Patent No.: US 12,767,779 B2
(45) Date of Patent: Oct. 20, 2026

(54) BACILLUS SUBTILIS SK01 AND ITS APPLICATION IN PLASTIC DEGRADATION

(71) Applicant: Bijie Shangkun plastic products Co., Ltd, Bijie (CN)

(72) Inventor: Shangkun Gu, Bijie (CN)

(73) Assignee: Bijie Shangkun plastic products Co., Ltd, Bijie (CN)

( * ) Notice: Subject to any disclaimer, the term of this patent is extended or adjusted under 35 U.S.C. 154(b) by 562 days.

(21) Appl. No.: 18/449,736

(22) Filed: Aug. 15, 2023

(65) Prior Publication Data

US 2023/0391979 A1 Dec. 7, 2023

Related U.S. Application Data

(63) Continuation of application No. PCT/CN2021/139199, filed on Dec. 17, 2021.

(30) Foreign Application Priority Data

Feb. 23, 2021 (CN) ......................... 202110200261.8

(51) Int. Cl.

| | |
|---|---|
| ***C12N 1/205*** | (2026.01) |
| ***B09B 3/60*** | (2022.01) |
| ***C08J 3/22*** | (2006.01) |
| ***C08J 11/10*** | (2006.01) |
| ***C12N 11/089*** | (2020.01) |
| *B09B 101/75* | (2022.01) |
| *C12R 1/125* | (2006.01) |

(52) U.S. Cl.

CPC ............... *C08J 11/105* (2013.01); *B09B 3/60* (2022.01); *C08J 3/226* (2013.01); *C12N 1/205* (2021.05); *C12N 11/089* (2020.01); *B09B 2101/75* (2022.01); *C08J 2305/00* (2013.01); *C08J 2323/06* (2013.01); *C08J 2405/00* (2013.01); *C08J 2483/04* (2013.01); *C12R 2001/125* (2021.05)

(58) Field of Classification Search

None

See application file for complete search history.

(56) References Cited

FOREIGN PATENT DOCUMENTS

| | | | |
|---|---|---|---|
| CN | 101921714 | A | 12/2010 |
| CN | 112375720 | A | 2/2021 |
| CN | 112852675 | A | 5/2021 |
| CN | 112939240 | A | 6/2021 |
| EP | 1849859 | A1 | 10/2007 |

*Primary Examiner* — David Steadman

(74) *Attorney, Agent, or Firm* — JEEN IP LAW, LLC

(57) ABSTRACT

*Bacillus Subtilis* SK01 and its application in plastic degradation. *Bacillus Subtilis* SK01 collected by China Center for Type Culture Collection (CCTCC), CCTCC NO: M2020812 is used to prepare a degradable plastic that can protect *Bacillus Subtilis* SK01 from the damage of high temperature and reduce the difference with polyene plastics in specific gravity. The plastic may be stored for more than 1 year to ensure that the microbial enzymes produced by *Bacillus Subtilis* SK01 can achieve 49.11% of total degradation of organic solids after 153 days in an environment for composting or soil burial, and can be slowly degraded by sunlight (photodegradation) or immersion in water. Under an environment other than that mentioned above, the finished products of polyene plastics added with *Bacillus Subtilis* SK01 are consistent with the non-degradable plastics in shelf life, satisfying the demand of a variety of polyene plastics.

3 Claims, 3 Drawing Sheets

BACILLUS SUBTILIS SK01 AND ITS APPLICATION IN PLASTIC DEGRADATION

CROSS-REFERENCE TO RELATED APPLICATIONS

The present application is a U. S. continuation of co-pending International Patent Application No. PCT/CN2021/139199 filed Dec. 17, 2021, which claims foreign priority of Chinese Patent Application No. 202110200261.8, filed on Feb. 23, 2021 in the State Intellectual Property Office of China, the contents of all of which are hereby incorporated by reference.

TECHNICAL FIELD

The disclosure relates to the field of microbial technology, in particular to a novel *Bacillus subtilis* (i.e., *Bacillus Subtilis* SK01) and its application in plastic degradation.

BACKGROUND

Plastic products have a bad reputation for white pollution. However, the products are also an indispensable supply for human civilized life, and the mother of industry as well. For this, biodegradable materials are springing up like mushrooms as people clamor for solving the problem of white pollution.

Biodegradable plastics refer to a type of plastics that may be degraded by microorganisms existing in nature, e.g., bacteria, molds (fungi) and algae. An ideal biodegradable plastic is a polymer material with excellent performance, which may be completely decomposed by environmental microorganisms after disposal, and eventually become an integral part of the carbon cycle in nature. “Paper” is a typical biodegradable material, while “synthetic plastics” are a typical polymer material. Therefore, biodegradable plastics are polymer materials with properties of both “paper” and “synthetic plastics”.

In large-scale use, cost should be the first consideration after all, and so, low-cost commercialization is to be achieved for the current research and development of biodegradable plastics.

SUMMARY

The object of the present disclosure is to provide *Bacillus Subtilis* SK01 with excellent characteristics as well as its application in the field of plastic degradation. The technical scheme for the disclosure is detailed as follows:

*Bacillus Subtilis* SK01, collected by China Center for Type Culture Collection, CCTCC NO: M2020812.

Biological Characteristics of *Bacillus Subtilis* SK01:

(1) This strain of *Bacillus subtilis* proliferates rapidly with a reproductive advantage as co-existing with other strains.

(2) Heat resistance:

1) Temperature and humidity of activity: temperature 15~85° C./humidity 30~100%;

2) Temperature and humidity of dormancy: temperature −60° C.~14° C., 86° C.~119° C./humidity 30~100%;

3) Temperature and humidity of death: temperature below −60° C., above 120° C./humidity 30~100%;

4) Temperature and humidity of death: temperature 340° C./humidity 0.01~0.2%/20 seconds.

| | Humidity | | | |
|---|---|---|---|---|
| | Humidity 30 to 100% | | | Humidity 0.01 to 0.2%(20 seconds) |
| Temperature | Activity | dormancy | Death | Death loss |
| Minimum °C | >15 | <−60~14 | >−60 | >−60 |
| Maximum °C | <85 | >86~119 | >120 | >340 |

(3) The spores have a high resistance to adversity, and at temperature and humidity of activity, bud rapidly.

(4) Extremely high capacity for decomposition of organic matter: with highly active enzymes for decomposing starch, protein, fat, cellulose, and etc.

(5) Extremely high capacity for inhibition of spoilage bacteria, foul-smelling bacteria and pathogenic bacteria: with antagonistic effect on pathogenic bacteria like *Staphylococcus aureus* (including MRSA), *salmonella*, coliform bacteria (including O157: H7), *dysenteriae, vibrio enteritidis, Pseudomonas aeruginosa, legionella* and plant pathogenic fungi like *fusarium*, alternarium, *botrytis*, pestalotia and etc.

The disclosure also provides the application of this *Bacillus subtilis* in degradation of plastics, especially polyene plastics.

For polyene plastics, a carrier of various microbial enzymes produced by *Bacillus Subtilis* SK01, after use, the corresponding plastic products are being aged, and as buried in soil or in compost, the polyene plastics release microbial enzymes produced by *Bacillus Subtilis* SK01 through immersion wetting and surface oxidation with acidic moisture, and thus induce environmental indigenous bacteria to grow and multiply on the body of plastic products, resulting in accelerated aging of plastic products. Then, through the environmental metazoan swallowing and metabolism, the plastics are decomposed or degraded finally. This effect is referred to as “bio-bento” of bioenergy reverse erosion carrier.

Preferably, for the above application, the amount of *Bacillus Subtilis* SK01 is 0.05~0.2% of the total weight of the plastic (0.5~2 kg/1000 kg).

The disclosure also provides a microparticle capsule characterized by a coat for *Bacillus Subtilis* SK01, which consists of lactic acid or chitosan and methyl silicone oil.

Preferably, the microparticle capsule of *Bacillus subtilis* contains 49~53% of *Bacillus Subtilis* SK01, 45~47% of lactic acid or chitosan, and 1~4% of methyl silicone oil (by weight percentage of dry solid form).

The disclosure also provides a method for preparation of the *Bacillus subtilis* microparticle capsule as follows: After mixing, drying, grinding, sifting and fine grinding of *Bacillus Subtilis* SK01 and the coat, add methyl silicone oil for compounding, thus forming a microparticle capsule with coated *Bacillus Subtilis* SK01.

Furthermore, the disclosure provides a biodegradable plastic masterbatch produced by banburying and granulation of the *Bacillus subtilis* microparticle capsule mentioned above, polyolefin, calcium carbonate, dispersant and zinc stearate.

Preferably, the biodegradable plastic masterbatch contains 0.3~1% of *Bacillus subtilis* microparticle capsule, 12~16% of polyolefin, 80~87% of calcium carbonate, 2% of dispersant, and 1% of zinc stearate (by weight percentage of dry solid form).

In addition, the disclosure provides a procedure for preparation of the biodegradable plastic masterbatch as follows:

(1) Stir and mix well the *Bacillus subtilis* microparticle capsule, polyolefin, calcium carbonate, dispersant and zinc stearate to obtain a mixture;

(2) After banburying of the mixture by an internal mixer, perform granulation by a screw extruder;

(3) Perform air cooling and sifting to obtain the product.

Preferably, in Step (2) of the above procedure, for banburying, the temperature is 170~202° C., and the duration is 25~35 minutes; for granulation of screw extruder, the temperature is 190~202° C., and the duration is 2~5 minutes. At the temperatures, the activity will not be lost or reduced.

This disclosure also provides a biodegradable plastic, which is made of the biodegradable plastic masterbatch and polyolefin material. The amount of added biodegradable plastic masterbatch is 5~50% of the total weight of biodegradable plastic.

Compared with the existing technology, this disclosure has the following advantageous effects:

*Bacillus Subtilis* SK01 can produce a variety of enzymes with high capacity for decomposition of organic matter, which is suitable for degradation of plastics and etc.

For the *Bacillus subtilis* microparticle capsule, lactic acid or chitosan is used for coating, and thus, the capsule can withstand 340° C./0.35 hr of high temperature without destruction of composition in an extremely anaerobic and high temperature environment, e.g., under dry and hot conditions, so that it can act as a degrading agent in the subsequent production of biodegradable plastics.

The biodegradable plastic masterbatch is used to prepare finished biodegradable plastics. The masterbatch can protect *Bacillus Subtilis* SK01 from the damage of high temperature and reduce the difference with polyene plastics in specific gravity. The plastic may be stored for more than 1 year to ensure that the microbial enzymes produced by *Bacillus Subtilis* SK01 can achieve 49.11% of total degradation of organic solids after 153 days in an environment for composting or soil burial, and can be slowly degraded by sunlight (photodegradation) or immersion in water. Under an environment other than that mentioned above, the finished products of polyene plastics added with *Bacillus Subtilis* SK01 are consistent with the non-degradable plastics in shelf life, satisfying the demand of a variety of polyene plastics.

DEPOSIT INFORMATION

Samples of *Bacillus Subtilis* SK01 (with a Latin name: *Bacillus Subtilis* SK01) has been deposited with China Center for Type Culture Collection of Wuhan University, Wuhan, China on Dec. 2, 2020 having the deposit number of CCTCC No: M2020812 under the terms of the Budapest Treaty on the International recognition of the Deposit of Microorganisms for the purpose of Patent Procedure.

DETAILED DESCRIPTION

Embodiments

Figure 1:
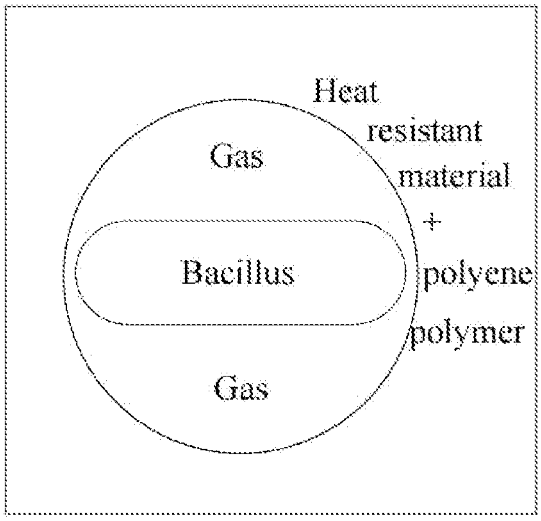
FIG. 1: The structure diagram of biodegradable plastic masterbatch.

Embodiment 1: Acquisition of *Bacillus Subtilis* SK01 and Relevant Characteristic Detection The native strain of *Bacillus Subtilis* SK01 adopted in the disclosure was taken from dry rice straw, and the procedure for screening is as follows:

1. Optimization of media and screening of conditions for culture of *Bacillus Subtilis* SK01

(1) C source basic medium: yeast extract 3 g/L, peptone 10 g/L, NaCl 5 g/L, pH 7.2-7.4.

(2) N source basic medium: glucose 5 g/L, NaCl 5 g/L, pH 7.2-7.4.

Culture the selected strain in C source basic medium, with glucose as the C source, prepare media with different glucose concentrations, and for each medium, dispense 25 mL in a 250 mL conical flask. Investigate the effects of glucose concentration on spore formation of the native strain.

With glucose concentration as the C source, to N source basic medium, add organic nitrogen: peptone, yeast extract, corn pulp powder, soybean powder, soybean cake powder, peanut cake powder, fish meal and yeast powder, 10.0 g/L each; inorganic nitrogen: urea, NH4Cl and (NH4)2 SO4, 20.0 g/L each. For each medium, dispense 25 mL in a 250 mL conical flask, and investigate the effects of different nitrogen sources on spore formation of the native strain.

To the optimized carbon source and nitrogen source media, add NaCl, CaCO3, MgSO4·7H2O, KH2PO4, K2HPO4, and K2HPO4+KH2PO4 respectively to prepare media. For each medium, dispense 25 mL in a 250 ml conical flask, and investigate the effects of different inorganic salts on spore formation of the native strain.

In the optimized media, the effects of inoculum size and aeration on the number of fermentation bacteria and the spore formation were investigated by a single factor test. With the pH value of media set at 7.0, for each medium, 25 mL was dispensed into a 250 ml conical flask, and inoculated with the strain with a spore rate above 90% screened in the preceding steps, so that the spores in the shake flasks achieved 104, 105, 106, and 107 orders of magnitude respectively. After 24 h of culture in the shake flask, the effect of inoculum size on the spore formation of *bacillus* was investigated. For each medium, 25 mL and 50 mL were separately dispensed into 250 mL shake flasks to investigate the effects of aeration on bacterial growth and spore formation.

After several rounds of screening, a strain of *Bacillus Subtilis* SK01 that could produce acidic enzymes under the activated condition of organic matter was obtained. The strain may produce a variety of proteases (especially alkaline protease), saccharase, lipase and amylase depending on the environmental nutrient sources.

A study found that *Bacillus Subtilis* SK01 was implanted in a polymer plastic, and affected by pH value or temperature change in the environment or ultraviolet radiation, the plastic was physically deteriorated, resulting in the release of

*Bacillus Subtilis* SK01 implanted in the polymer plastic due to the deterioration of carrier (For example: After the food package is broken, the food may go moldy for mold parasitism). The released *Bacillus Subtilis* SK01 rapidly expands and grows with organic matter in the environment as the nutrient source. There are different kinds of organic matter in the environment, and therefore, the biological enzymes formed after conversion are diverse. For the polymer originally used as the carrier of *Bacillus Subtilis* SK01, the organic matter that enters the nutritional food chain synchronously is decomposed into carbon dioxide, inorganic salts, and water at last. As protected by excipients, *Bacillus Subtilis* SK01 may own high temperature resistance as well as properties that contribute to plastic foaming.

The name under Classification and Nomenclature for Collection is *Bacillus Subtilis* SK01.

Embodiment 2: Preparation and Degradation Detection of Biodegradable Plastics

1. Preparation of *Bacillus subtilis* Microparticle Capsule

The mixed *Bacillus Subtilis* SK01 microorganism (49~53% by weight percentage of solid matter) and chitosan (45~47% by weight percentage of solid matter) underwent the following process: 43-45° C. low temperature→drying-grinding→1250~1500 mesh screening→fine grinding (to sub-micron level, 10-8 m)→adding methyl silicone oil (1~4% by weight percentage of solid matter) for compounding→completion of coating→*Bacillus subtilis* microparticles capsule.

Chitosan may be obtained from shrimp and crab chitosans after acid dissolution or purchased directly. It is characterized by high temperature resistance and polymer formation at a high temperature. After mixed with *Bacillus Subtilis* SK01, it can effectively protect the activity of *Bacillus Subtilis* SK01 from being lost at a temperature below 340° C.

Adding methyl silicone oil for compounding is to prevent the mixture of *Bacillus Subtilis* SK01 and chitosan from volatilization when the powder reaches the sub-micron level (10-8) after low temperature drying→grinding→sifting→fine grinding. The temperature for decomposition of methyl silicone oil is about 316° C., and with the increasing substitution of methyl group by propyl group, the decomposition temperature is also increasing. When the content of propyl group is 30%, the decomposition temperature is up to 400° C.

Because the plastic products need a high temperature above 170° C. for melting and polymerizing in the preparation process, with chitosan polymer as a parasitic carrier, methyl silicone oil is used for coating, thus achieving high dispersion, high cohesion and high temperature resistance to protect their activity from being lost.

*Bacillus subtilis* microparticle capsule can withstand 340° C./0.35 hr of high temperature without destruction of composition under dry and hot conditions.

2. Preparation of Biodegradable Plastic Masterbatch

Place 0.3~1% of *Bacillus subtilis* microparticle capsule, 12~15% of polyolefin resin plastic, 75~81% of calcium carbonate powder with fineness above 1250 mesh, 2% of dispersant and 1% of zinc stearate in a bucket, stir and mix well.

Send the mixture to an internal mixer at high temperature for 25~35 minutes of banburying under 170~202° C., and then perform 2~5 min of granulation by a screw extruder at 190~202° C. to obtain grains.

The biodegradable plastic masterbatch may be obtained after air cooling, sifting, aggregating, weighing and bagging of the grains.

Figure 2:
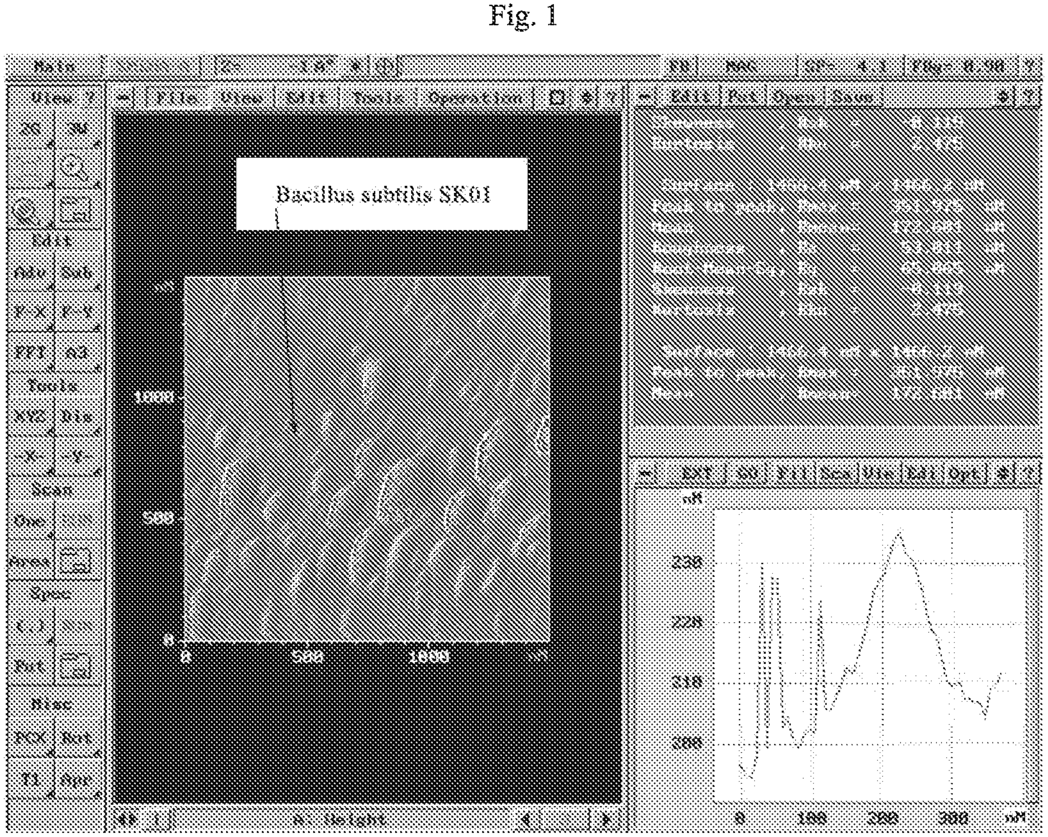
FIG. 2: The 3D tunnel photograph of *Bacillus Subtilis* SK01 in a plastic product.
Figure 3:
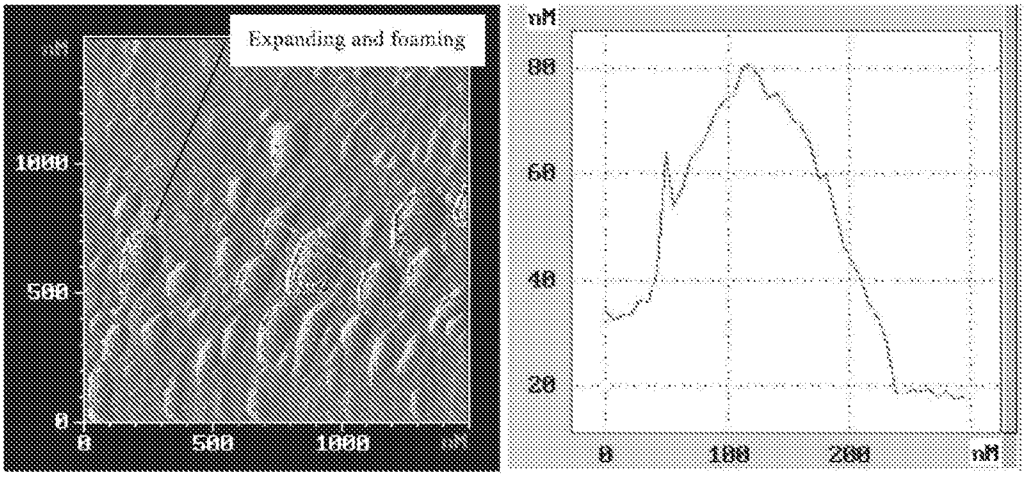
FIG. 3: The 3D tunnel photograph of expanded foam of plastic caused by the interaction of microbial enzymes produced by *Bacillus Subtilis* SK01 with the plastic.
Figure 4:
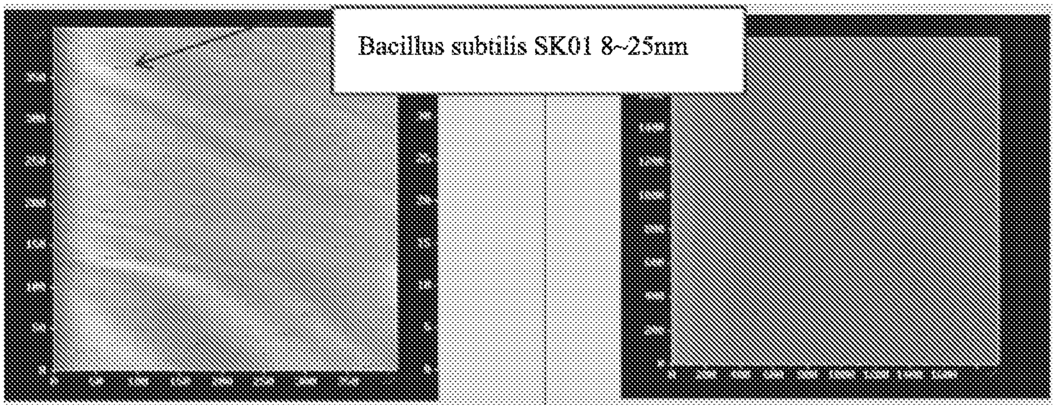
FIG. 4: The size of *Bacillus Subtilis* SK01 in a plastic product (3D tunnel photograph)

As shown in FIG. 1, the microstructure of biodegradable plastic masterbatch is in a form of balloon encapsulation. In the preparation process, *Bacillus Subtilis* SK01 absorbs gas itself, and the gas is blocked by polymer due to banburying and melting, thus forming a balloon foam. As the temperature increases, the balloon is further inflated while *Bacillus Subtilis* SK01 in the balloon floats in the gas. When *Bacillus Subtilis* SK01 approaches the high temperature of balloon wall, it moves to the space at a lower temperature instinctively. Please refer to FIGS. 2-4, where the 3D tunnel photographs show that the balloon volume is 200 to 250 nm, while the volume of *Bacillus Subtilis* SK01 is 8 to 25 nm. Therefore, the gas in the balloon can maintain *Bacillus Subtilis* SK01 at a constant body temperature at high temperatures indirectly or directly, and through physical regulation, reduce the effect of temperature on *Bacillus Subtilis* SK01, or even its loss.

The biodegradable plastic masterbatch may reduce the difference with polyolefin plastics in specific gravity. During the banburying and melting process of *Bacillus Subtilis* SK01 and polyolefin resin plastic, the oxygenophilic expansion and growth at 65° C.~75° C. make polyene plastics produce microbubbles, resulting in expanding and foaming of polyene plastics. Under the same volume, the specific gravity of polyene plastics added with *Bacillus Subtilis* SK01 is 0.919~0.926, which is 0.04 lower than polyene plastics without *Bacillus Subtilis* SK01 (specific gravity: 0.923~0.93).

Relevant detection found that the plastics made of biodegradable plastic masterbatch achieved 49.11% of total degradation of organic solids after 153 days in an environment for composting or soil burial, and were slowly degraded by sunlight (photodegradation) or immersion in water. Under an environment other than that mentioned above, the plastics made of biodegradable plastic masterbatch are consistent with the non-degradable plastics in shelf life, which is more than 1 year.

3. Degradation Detection

The biodegradable plastic masterbatch may be used to manufacture polyene products, e.g., films, bags, blister products, hard plastics, or adjust the dosage of polyolefin materials between 50~95% and of biodegradable plastic masterbatch between 5~50% depending on the physical demands. The values and value ranges in percentage in this embodiment are all by weight percentage.

According to three experiments, each two-year verification (certified by Plastic Products Quality Supervision and Inspection Center (Beijing), GSJ C0292) showed that polyolefin materials add with more than 5% of biodegradable plastic masterbatch may induce the performance of biodegradable polyolefin organics, and the proportion for addition is inversely proportional to the physical demand. The more the biodegradable plastic masterbatch, the stronger the induced biodegradability, and the poorer the transverse/longitudinal tension and extension force as physical properties. According to a physical test, with 0.008 mm of plastic film thickness and 5% of masterbatch proportion as the base points, for every 0.001 mm increment, the addition ratio can be increased by 1~ 1.2%, with 50% as the upper limit.

For a 0.035 mm diaphragm specimen made of 54% of finished polyolefin material and 46% of biodegradable plastic masterbatch, the 153-day polyolefin degradation rate of polyolefin material (with calcium carbonate as the inorganic matter) reached 90.9%. The reference material was cellulose.

TABLE 1

Basic characteristics of the specimen

| Sample | Appearance | Dry solid Content | Water Content | Total organic carbon in dry solids | Theoretical carbon dioxide release ($CO_2$ g/100 g dry sample) |
|---|---|---|---|---|---|
| Specimen | diaphragm | 98.48% | 1.52% | 58.90% | 215.97 |
| Reference material | Powder | 99.06% | 0.94% | 43.03% | 157.78 |

TABLE 2

Carbon dioxide release and bio-decomposition rate

| Days | $CO_2$ release of blank test, g | $CO_2$ release of reference material, g | Bio-decomposition rate of reference material, % | $CO_2$ release of specimen, g | Bio-decomposition rate of specimen, % |
|---|---|---|---|---|---|
| 153 | 56.0 | 149.3 | 94.6 | 106.1 | 49.1 |

(0.01~0.1 mm), which are swallowed and digested by the ecological metazoan, and at last, converted into carbon dioxide, water and calcium carbonate or reduced to harmless substances in the ecological environment.

The products added with biodegradable plastic masterbatch passed tests of FDA and RoHS, tests for 12 heavy metals, 21 chemical toxicity tests, yellowing level 4 test, and the highest-level test of horizontal and longitudinal tension, and thus, a relevant high-quality evaluation on degradation performance, safety and physical properties was obtained.

For the products added with biodegradable plastic masterbatch, the test results of lead, cadmium, mercury, hexavalent chromium, polybrominated biphenyl (PBB), polybrominated diphenyl ether (PBDE) were within the limits specified in Appendix II of Directive 2011/65/EU as revision of RoHS Directive 2002/96/EC (EU).

According to the regulatory requirements of the US FDA, the maximum extractable amount of polyethylene in biodegradable plastic masterbatch as a component used for coating in contact with food was determined. For the test method, refer to US FDA 21 CFR 177.1520 d(3)(ii) &d(4)(ii). The test results are as follows:

TABLE 3

Carbon dioxide output and bio-decomposition rate

| | $CO_2$ output, g | | | | | Decomposition rate, % | |
|---|---|---|---|---|---|---|---|
| Days | Blank | Cellulose | 2012E0568 Specimen | Cellulose (actual) | 2012E0568 Specimen | Cellulose | 2012E0568 Specimen |
| 0 | 0.00 | 0.00 | 0.00 | 0.00 | 0.00 | 0.00 | 0.00 |
| 10 | 15.04 | 34.53 | 26.15 | 19.49 | 11.11 | 12.35 | 5.14 |
| 20 | 41.29 | 72.17 | 54.31 | 30.88 | 13.02 | 19.57 | 6.03 |
| 30 | 51.18 | 109.01 | 81.86 | 57.83 | 30.68 | 36.65 | 14.21 |
| 40 | 52.84 | 150.88 | 113.18 | 98.04 | 60.34 | 62.14 | 27.94 |
| 50 | 53.14 | 171.81 | 128.83 | 118.67 | 75.69 | 75.21 | 35.05 |
| 60 | 53.44 | 179.70 | 135.77 | 126.26 | 82.33 | 80.02 | 38.12 |
| 70 | 53.73 | 187.59 | 145.94 | 133.86 | 92.21 | 84.84 | 42.70 |
| 80 | 54.03 | 195.49 | 151.64 | 141.46 | 97.61 | 89.66 | 45.20 |
| 90 | 54.33 | 201.34 | 153.97 | 147.01 | 99.64 | 93.17 | 46.14 |
| 100 | 54.62 | 202.87 | 154.91 | 148.25 | 100.29 | 93.96 | 46.44 |
| 110 | 54.92 | 203.45 | 156.55 | 148.53 | 101.63 | 94.14 | 47.06 |
| 120 | 55.21 | 203.90 | 159.89 | 148.69 | 104.68 | 94.24 | 48.47 |
| 130 | 55.46 | 204.35 | 161.14 | 148.89 | 105.68 | 94.37 | 48.93 |
| 140 | 55.68 | 204.80 | 161.59 | 149.12 | 105.91 | 94.51 | 49.04 |
| 150 | 55.95 | 205.25 | 161.97 | 149.30 | 106.02 | 94.63 | 49.09 |
| 153 | 56.05 | 205.38 | 162.12 | 149.33 | 106.07 | 94.64 | 49.11 |

Figure 5:
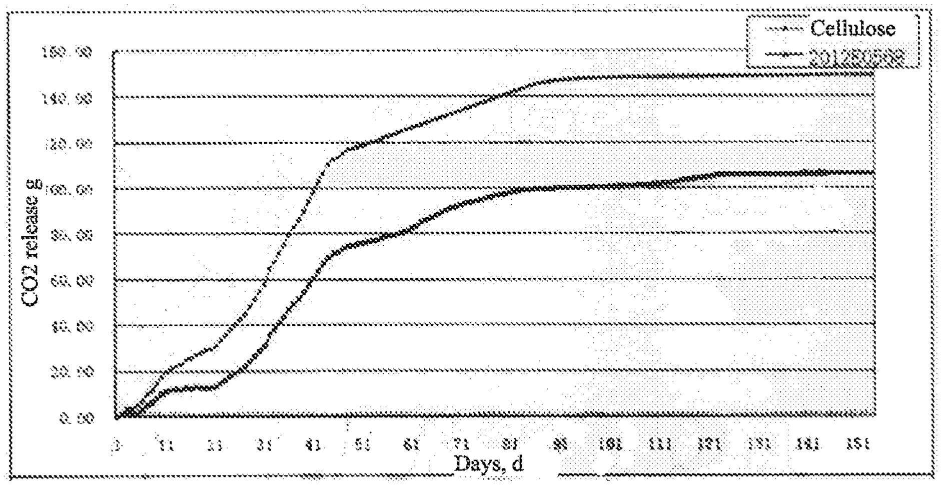
FIG. 5: The carbon dioxide release curve during the cellulose degradation of 2012E0568 specimen and reference material.
Figure 6:
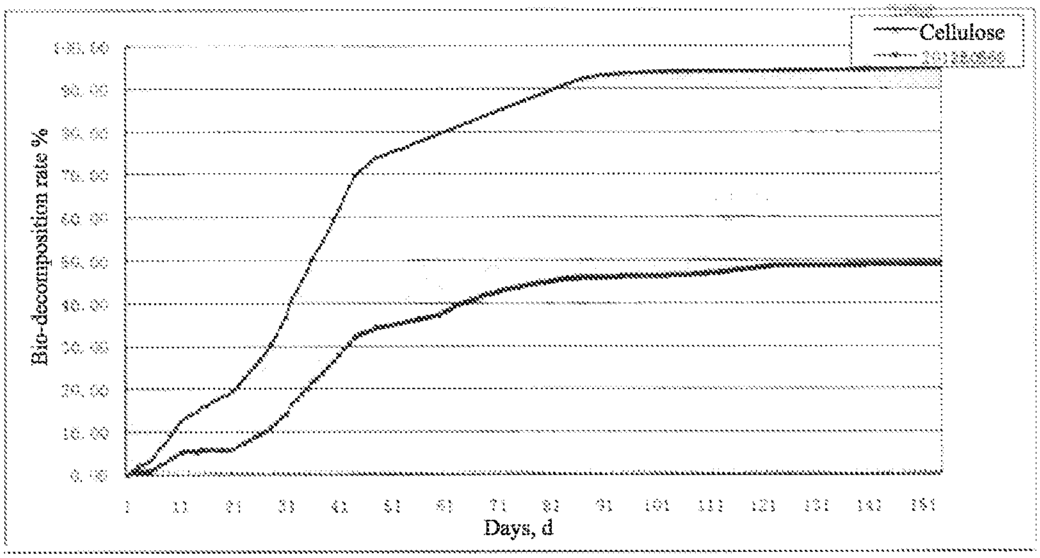
FIG. 6: The biological decomposition curve during the cellulose degradation of 2012E0568 specimen and reference material.

FIG. 5 shows the carbon dioxide release curves of 2012E0568 specimen and cellulose as the reference material during degradation.

The biodegradable plastic masterbatch of this disclosure induces biodegradable polyolefin polymer based on the polyolefin material implanted with highly processed *Bacillus Subtilis* SK01 as the main principle of action. With high temperature resistance, the components of *Bacillus Subtilis* SK01 will not be destroyed at high temperatures for granulation, extrusion, injection, film formation or bagging. After use, the bags and films are buried in the soil or compost, and microbial enzymes produced through the growth and proliferation of *Bacillus Subtilis* SK01 induce indigenous bacteria to gather and decompose, so that the bags and films are cracked into fine sheets (4~5 cm), and through ecological chemical chelation, decomposed into powder particles

| Conventional simulation solution | Time | Temperature | Maximum allowable limit | Detection value of sample |
|---|---|---|---|---|
| N-hexane | 2 hr | 50 °C | 53% (w/w) | 3.7 (w/w) |
| xylene | 2 hr | 25 °C | 75% (w/w) | 5.7 (w/w) |

The packing bag added with biodegradable plastic masterbatch is 700±5 mm long and 510±5 mm wide with bilateral stitches. The number of monofilaments within 100 mm is no less than 47. The mechanical performance test results and physical properties are as shown in the following table:

| Mass per unit area ($g/m^2$) | Tensile load (N/50 mm) not less than | | | | | Peel force (N, 30 mm) |
|---|---|---|---|---|---|---|
| | In the radial direction | In the zonal direction | In the direction of adhesion | In the direction of hemming | In the direction of hemming bottom | |
| ≥75 | 450 | 450 | 300 | 250 | 200 | ≥3.0 |

Firmness: With 5 packing bags randomly selected, the failure rate after 2.5 m±2 mm high altitude free fall: ≤4.

The temperature applicable for the packing bags: ≥100° C.

The influence of paper bag material on cement strength: 3-day flexural strength ratio ≥93%, 3-day compressive strength ratio ≥95%.

Moisture-proof performance of the packing bags: 3-day compressive strength ratio ≥90%.

The tensile test results of monofilament: At least 80% passed the tension test of monofilament.

The packing bags prepared with biodegradable plastic masterbatch and polyethylene as raw materials, the product inspection results based on GB13735-92 standard are as shown in the following table:

| Name | Item | Standard requirements | Inspection results | Individual evaluation |
|---|---|---|---|---|
| Specification | Width limit deviation, mm | ±15 | +8 | Superior quality |
| | Thickness limit deviation, % | ±0.002 | +0.002 | Superior quality |
| | Average thickness deviation % | ±10 | +5 | Superior quality |
| | Average thickness, mm | 0.008 | 0.0084 | Superior quality |
| Appearance | Watermark and cloud | Does not affect use | There is no | Superior quality |
| | Bubble perforation and rupture | There is no | There is no | Superior quality |
| | Impurities, fish eyes and stiff blocks | See Standards for details | There is no | Superior quality |
| | Streaks and tears | Flat tears should not form straight lines | There is no | Superior quality |
| | Roll paper core for diaphragm exposed | 20 ± 5 mm | 24 | Superior quality |
| | Folding and misalignment | | There is no | Superior quality |
| | Bulges | Not allowed | There is no | Superior quality |
| Physical property Mass per unit area | Tensile load, N | Longitudinal/transverse ≥ 1.6 | 2.2/2.0 | Superior quality |
| | Elongation at break, % | Longitudinal/transverse ≥ 160 | 448/672 | Superior quality |
| | Right angle load, N | Longitudinal/transverse ≥ 0.6 | 1.2/1.5 | Superior quality |
| | Tensile load, N | Longitudinal/transverse≥ | // | // |
| | Elongation at break, % | Longitudinal/transverse≥ | // | // |
| | Right angle load, N | Longitudinal/transverse≥ | // | // |
| Functional performance | Light transmittance, % | // | // | // |
| | Haze, % | // | // | // |
| Conclusion | | | | Superior quality |

Different from grain based materials (The main biodegradable plastics based on natural substances like starch include the following products: polylactic acid (PLA), polyhydroxyalkanoate (PHA), starch plastics, bioengineering plastics, biological general-purpose plastics like polyolefin and polyvinyl chloride, and etc.), the biodegradable plastic masterbatch, with the mechanism of inducing biodegradable polyene polymer, may be used to produce biodegradable plastic products without any change, increase or modification of production process or equipment. The products own a strong market competitiveness due to the affordable cost.

This document has utilized specific cases to elaborate the inventive concept, while the above embodiments are only to help understand the core idea of the disclosure. It should be noted that for ordinary technical personnel in the field, any significant modification, equivalent replacement, or other improvements without deviation from the conception of the disclosure shall be included in the scope of protection for the disclosure.

What is claimed is:

1. A biodegradable plastic masterbatch produced by mixing and granulating a *Bacillus subtilis* microparticle capsule, polyolefin, calcium carbonate, dispersant and zinc;

wherein the *Bacillus subtilis* microparticle capsule comprises *Bacillus Subtilis* SK01 coated with a coating consisting of lactic acid and methyl silicone oil or a coating consisting of chitosan and methyl silicone oil;

wherein the *Bacillus Subtilis* SK01 is deposited at the China Center for Type Culture Collection (CCTCC) with the deposit number CCTCC M2020812.

2. The biodegradable plastic masterbatch according to claim 1;

wherein the microparticle capsule is dry solid, and the weight percent of the total weight of the dry solid for each component is: 49-53% of the *Bacillus Subtilis* SK01, 45-47% of the lactic acid or chitosan, and 1-4% of the methyl silicone oil of the total weight of dry solid.

3. The biodegradable plastic masterbatch according to claim 1, wherein the biodegradable plastic masterbatch is a dry solid, and wherein the wight percent of the total weight of the dry solid for each component is: 0.3~1% of the *Bacillus subtilis* microparticle capsule, 12~16% of polyolefin, 80~87% of calcium carbonate, 2% of dispersant, and 1% of zinc stearate.

* * * * *